(12) United States Patent
Kim

(10) Patent No.: US 11,100,263 B2
(45) Date of Patent: Aug. 24, 2021

(54) METHOD OF PREDICTING SUGAR CONTENT AND ACIDITY OF FRUIT USING MULTIVARIATE STATISTICAL ANALYSIS OF FT-IR SPECTRUM DATA

(71) Applicant: JEJU NATIONAL UNIVERSITY INDUSTRY—ACADEMIC COOPERATION FOUNDATION, Jeju (KR)

(72) Inventor: In-Jung Kim, Jeju (KR)

(73) Assignee: JEJU NATIONAL UNIVERSITY INDUSTRY-ACADEMIC COOPERATION FOUNDATION, Jeju-si (KR)

(*) Notice: Subject to any disclaimer, the term of this patent is extended or adjusted under 35 U.S.C. 154(b) by 772 days.

(21) Appl. No.: 15/320,950

(22) PCT Filed: Jun. 26, 2015

(86) PCT No.: PCT/KR2015/006580
§ 371 (c)(1),
(2) Date: Dec. 21, 2016

(87) PCT Pub. No.: WO2015/199495
PCT Pub. Date: Dec. 31, 2005

(65) Prior Publication Data
US 2017/0199952 A1    Jul. 13, 2017

(30) Foreign Application Priority Data
Jun. 26, 2014 (KR) .................. 10-2014-0078834

(51) Int. Cl.
*G06F 17/10* (2006.01)
*G06F 30/20* (2020.01)
(Continued)

(52) U.S. Cl.
CPC .......... *G06F 30/20* (2020.01); *G01N 33/0098* (2013.01); *G06F 17/14* (2013.01); *G06F 17/18* (2013.01)

(58) Field of Classification Search
CPC .......... A01H 5/08; A01H 1/04; G01N 21/359; G01N 21/3563; G01N 33/025;
(Continued)

(56) References Cited

U.S. PATENT DOCUMENTS 8,048,317 B2 * 11/2011 Rima ................... C02F 1/725
210/763
2011/0307187 A1 * 12/2011 Watari ................. G01J 3/457
702/32

(Continued)

OTHER PUBLICATIONS

Duarte et al. Application of FTIR Spectroscopy for the Quantification of Sugars in Mango Juice as a Function of Ripening J. Agric. Food Chem. 2002, 50, 3104-3111 (Year: 2002).*

(Continued)

*Primary Examiner* — Rehana Perveen
*Assistant Examiner* — Cuong V Luu
(74) *Attorney, Agent, or Firm* — Lex IP Meister, PLLC

(57) ABSTRACT

Disclosed is a method of predicting a sugar content and acidity of fruits that is capable of predicting a sugar content and acidity of ripe fruits before harvest using samples of unripe fruits. The predicted sugar content and acidity can be used as data for quality management of fruits, such as output control of fruits, before the fruits become fully ripe. In addition, the predicted sugar content and acidity can be used as data for selection of candidate seeds, so that efficiency of development of new varieties can be improved.

5 Claims, 4 Drawing Sheets

(51) Int. Cl.
  *G06F 17/18* (2006.01)
  *G01N 33/00* (2006.01)
  *G06F 17/14* (2006.01)
(58) Field of Classification Search
  CPC .... G01N 33/02; G01N 21/35; G01N 2201/12; G01N 2021/3595; G06F 19/00; C02F 1/72
  See application file for complete search history.

(56) References Cited

U.S. PATENT DOCUMENTS

2014/0183362 A1* 7/2014 Islam .................. G01J 3/453
    250/338.4
2016/0047787 A1* 2/2016 Islam .................. G01J 3/453
    600/322

OTHER PUBLICATIONS

Bureau et al. Application of ATR-FTIR for a rapid and simultaneous determination of sugars and organic acids in apricot fruit Food Chemistry 115, pp. 1133-1140 (Year: 2009).*

Li et al. Quantitative Analysis of Individual Sugars and Acids in Orange Juices by Near-Infrared Spectroscopy of Dry Extract J. Agric. Food Chem 1996, 44, pp. 2252-2259 (Year: 1996).*

Bureau et al. Determination of the Composition in Sugars and Organic Acids in Peach Using Mid Infrared Spectroscopy: Comparison of Prediction Results According to Data Sets and Different Reference Methods; Analytical Chemistry, ACS Publications, pp. 11312-11318 (Year: 2013).*

Song et al. Establishment of rapid discrimination system of leguminous plants at metabolic level using FT-IR spectroscopy with multivariate analysis J Plant Biotechnol, 2012 39:121-126 (Year: 2012).*

Song et al. (translated version of the Korean NPL) Establishment of rapid discrimination system of leguminous plants at metabolic level using FT-IR spectroscopy with multivariate analysis J Plant Biotechnol, 2012 39:121-126 (Year: 2012).*

Magwaza et al. NIR Spectroscopy Applications for Internal and External Quality Analysis of Citrus Fruit—A Review, Food Bioprocess, 2012 5: pp. 425-444 (Year: 2012).*

Coimbra et al. Multivariate Analysis of Uronic Acid and Neutral Sugars in Whole Pectic Samples by FT-IR Spectroscopy Carbohydrate Polymers 37, 1998, pp. 241-248 (Year: 1998).*

* cited by examiner

[FIG. 1]
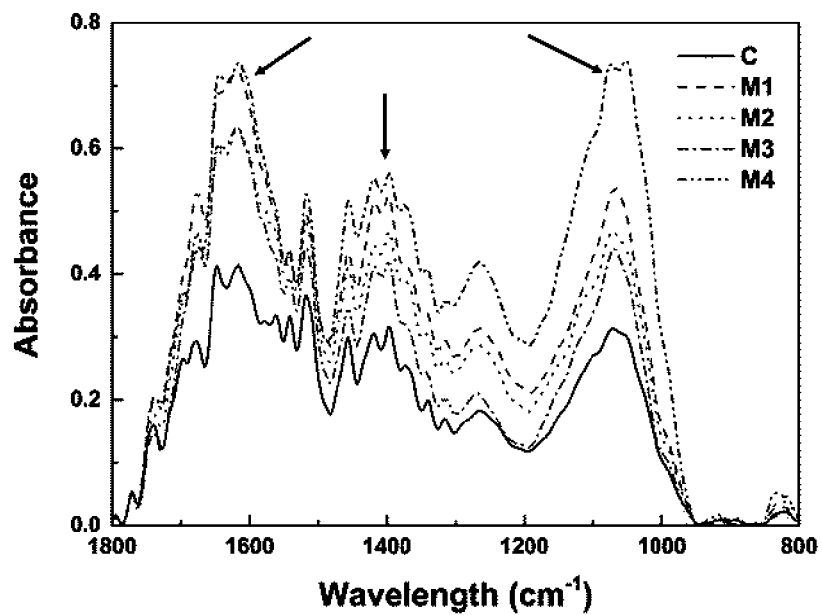
[FIG. 2]
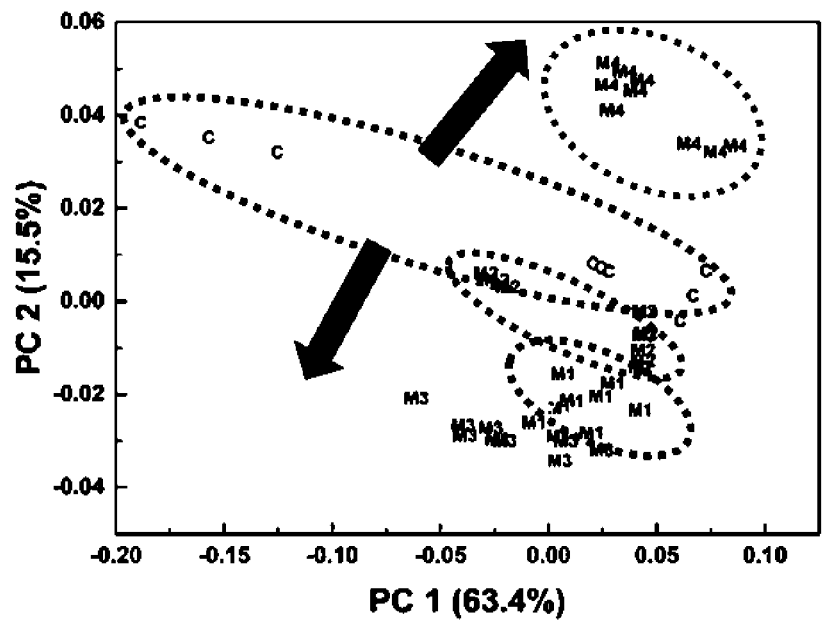

[FIG. 3]
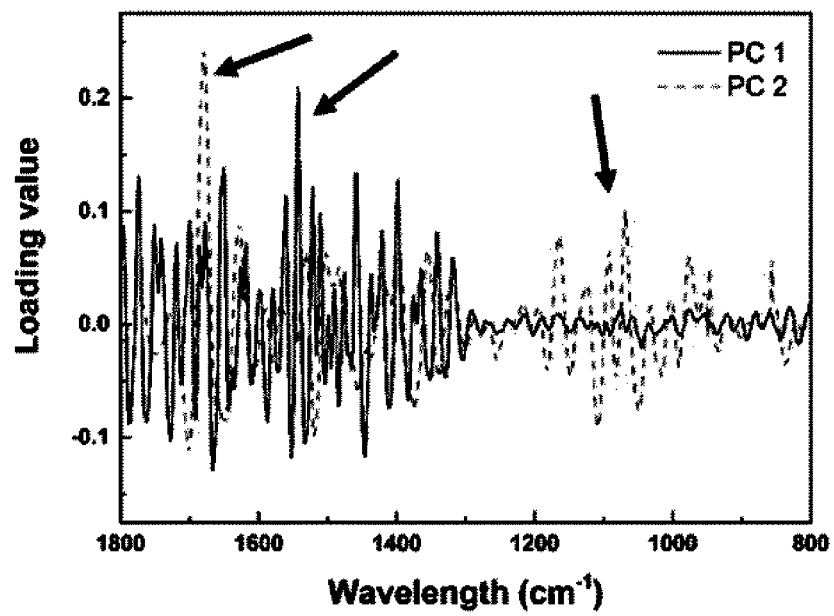
[FIG. 4]
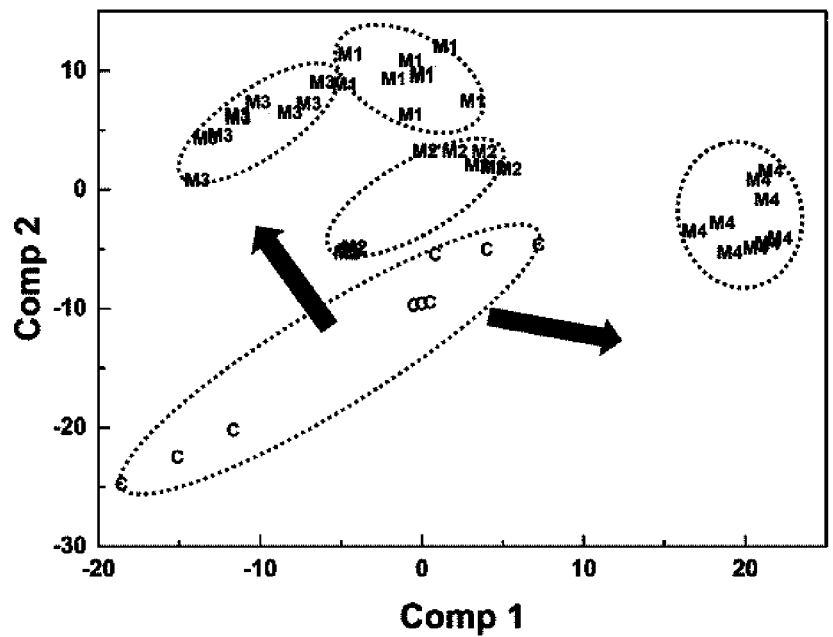

[FIG. 5]
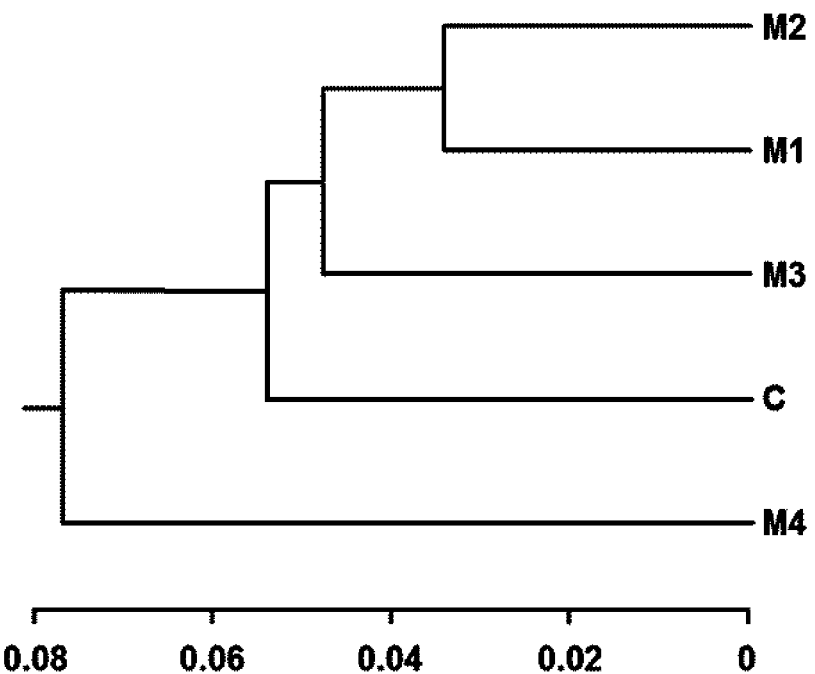
[FIG. 6]
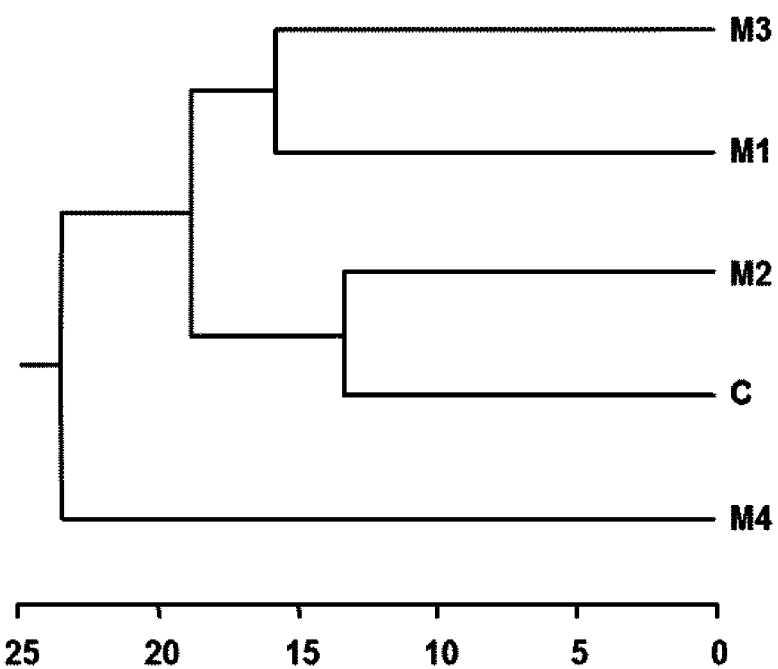

[FIG. 7]
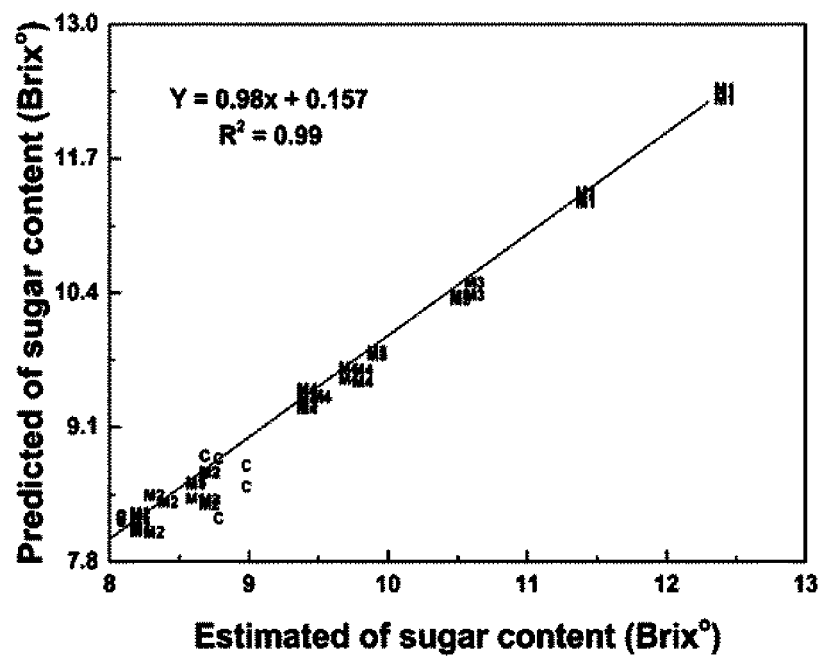
[FIG. 8]
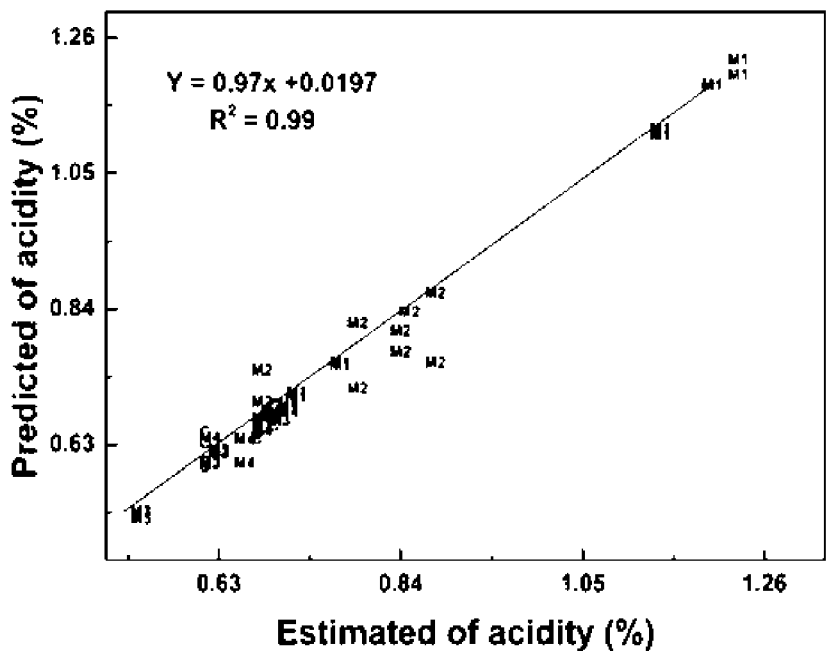

METHOD OF PREDICTING SUGAR CONTENT AND ACIDITY OF FRUIT USING MULTIVARIATE STATISTICAL ANALYSIS OF FT-IR SPECTRUM DATA

TECHNICAL FIELD

The present invention relates to a method of predicting sugar content and acidity of ripe fruits from samples of unripe fruits using multivariate statistical analysis results of FT-IR spectral data.

BACKGROUND ART

Jeju island has produced 600 billion Won or more of citrus fruit per year since 2008 and citrus fruit yields a high output corresponding to the first quarter or more of the total domestic fruit production. Recently, trade liberalization resulting from the conclusion of FTAs with China, Japan, the US and the EP has brought about an increase in import of citrus fruits and the survival of the domestic citrus fruit industry is thus threatened. In an attempt to overcome these problems, development of novel varieties of fruits such as citrus fruits has been attempted and management of quality, such as sugar content and acidity, and of output of grown fruits is required.

In accordance with a Fourier transform infrared (FT-IR) analysis method, when molecules in a sample absorb infrared (IR) light emitted to the sample and then vibrate, characteristic infrared spectra corresponding to this vibration energy are generated and information on the sample can be obtained by analyzing the spectra. This method has an advantage of using a variety of information of spectrum (Non-patent document 1).

Partial least squares (PLS) regression, as one of multivariate statistical analysis methods, is used in modeling to predict contents of a variety of ingredients by analyzing the correlation between accurate quantitative analysis data of a sample and spectral data of the sample (Non-patent document 2).

(Prior Art Document, Non-Patent Document)

1. Krishnan, P., N. J. Kruger, and R. G. Ratcliffe. 2005. Metabolite fingerprinting and profiling in plants using NMR. J. Exp. Bot. 56:255-265.

2. Wold, S., M. Sjostrom, and L. Eriksson. 2001. PLS-regression: a basic tool of chemometrics. Chemometrics and Intelligent Lab. Systems 58:109-130.

DISCLOSURE

Technical Problem

Therefore, the present invention has been made in view of the above problems, and it is an object of the present invention to provide a method of predicting sugar contents and acidity of ripe fruits using data obtained from unripe fruit samples.

Technical Solution

This application claims under 35 U.S.C. § 119(a) the benefit of priority to Korean Patent Application No. 2014-0078834 filed on Jun. 26, 2014, the entire contents of which are incorporated herein by reference.

Hereinafter, the present invention will be described in more detail.

As used herein, the terms "sugar content/acidity" mean "sugar content and acidity".

As a result of application of multivariate statistical analysis to FT-IR spectral data of unripe fruits using citrus fruits, the inventors of the present invention found that a system for rapidly classifying and identifying qualities of fruits at a harvest time can be established, and completed the present invention based on this finding.

In accordance with an aspect of the present invention, the above and other objects can be accomplished by the provision of a method of predicting sugar contents or acidity of fruits including preparation of obtaining a sample for measuring spectrum from unripe fruits, measurement of obtaining Fourier transform infrared spectroscopy (FT-IR) spectral data of the unripe fruits using the sample for measuring spectrum, and prediction of applying the spectral data of unripe fruits to a predictive model of sugar contents or acidity based on multivariate statistical analysis previously prepared in a database to output a predicted value corresponding to a sugar content or acidity when the unripe fruits become ripe.

The preparation is a step of obtaining the sample for measuring spectrum from unripe fruits and is performed by i) lyophilizing the unripe fruits to obtain dried unripe fruits and pulverizing the dried unripe fruits to obtain a sample for preparing an extract, and ii) applying an extraction solvent to the sample for preparing an extract to obtain an extract of unripe fruits and removing solids to obtain a sample for measuring spectrum.

The dried unripe fruits may be obtained by drying whole cells of the unripe fruits by lyophilisation and the drying is preferably carried out by lyophilisation because damage to organic substances present in the unripe fruits can be minimized.

The extraction solvent is preferably the same as the extraction solvent used to establish the predictive model of sugar contents or acidity and is for example an alcohol having 1 to 5 carbon atoms, a solution containing the alcohol or the like, but the present invention is not limited thereto.

The FT-IR spectral data is for example obtained using a detector such as Tensor 27 (Bruker Optics GmbH, Ettlingen, Germany) and DTGS (deuterated triglycine sulfate) and can be obtained from results measured at a predetermined interval in an analysis region including a region of 1,800 to 800 $cm^{-1}$, the predetermined interval is for example an interval of $cm^{-1}$, and an average spectrum of values obtained by repeatedly measuring two or five times under the same conditions can be used as FT-IR spectral data in the subsequent step.

The method of predicting sugar contents or acidity of fruits may further include pre-processing the FT-IR spectral data to obtain standardized spectral data (standardization), between the measurement and the prediction.

This step is required to minimize experimental errors and may be carried out using an R program (version 2.15.0, Auckland, New Zealand), but may be used without any limitation so long as the pre-processing of spectral data is possible.

Specifically, the pre-processing in the standardization may include correcting an analysis region and a baseline of the FT-IR spectral data of unripe fruits to be identical to an analysis region and a baseline of spectral data of a training set used to establish the predictive model of the sugar content or acidity, normalizing an area of the corrected FT-IR spectral data of unripe fruits to be identical to an area of the spectrum applied to the training set, and conducting mean centering and quadratic differential processing on the normalized FT-IR spectral data of unripe fruits to obtain spectral data of unripe fruits.

The multivariate statistical analysis may include principal component analysis (PCA) and/or partial least squares discriminant analysis (PLS-DA).

The predictive model of the sugar content or acidity is a previously established modeling result stored in a database and means a model for predicting sugar contents and acidity of ripe fruits from measured variables by multivariate statistical analysis based on spectral data of unripe fruits, and sugar content and acidity data of ripe fruits derived from the same tree.

The predictive model of the sugar content or acidity may be established by applying data of a training set to partial least squares (PLS) modeling. For example, the predictive model of the sugar content or acidity may be prepared using FT-IR spectrum partial least squares regression algorithms and specifically, may be obtained by conducting partial least squares (PLS) modeling using data of a training set in a R program using NIPALS algorithms.

The training set used herein means a set of spectral data of unripe fruits and measured sugar content and acidity values of ripe fruits when the unripe fruits become ripe.

The predictive model of sugar content or acidity established using the training set can be obtained by applying spectral data of unripe fruits to an X variable, and a sugar content or acidity of ripe fruits measured when the unripe fruits become ripe to a Y variable ($Y_1$ or $Y_2$), respectively.

In this case, "of the ripe fruits measured when the unripe fruits become ripe . . ." means that the unripe fruits and the ripe fruits have substantially same properties only except for the harvest time of the fruits, for example, ripe fruits are harvested from the same trees as the harvested unripe fruits.

The predictive model of the sugar content or acidity may be previously prepared by a method of establishing a predictive model of the sugar content or acidity of fruits, which will be described later, and then stored in a database.

As a result of regression of the predictive model of the sugar content or acidity using a test set, the correlation coefficient ($R^2$) of the sugar content is 0.99, the correlation coefficient ($R^2$) of the acidity is 0.99 and predicted sugar content and acidity values of fruits upon ripening of unripe fruits, output in the prediction step, have about 90% or more of an accuracy as compared to true sugar content and acidity values when unripe fruits become ripe, which means that prediction accuracy is excellent.

Fruits mean edible sweet or sour fruits obtained from plants such as trees and specifically include, but are not limited to, pome fruits such as apples and pears, semi-pome fruits such as persimmons and tangerines, stone fruits such as peaches, plums and apricots, and berry fruits such as grapes.

The fruits may be any one selected from the group consisting of citrus fruits which belong to the genus Rutaceae (*Poncirus*, citrus fruits, citrus japonica), grapes, apples, kiwi, peaches, and pears. In this case, the prediction method of the present invention is highly applicable because it takes a relatively long time for unripe fruits to become ripe.

The citrus fruits may be any one selected from the group consisting of oranges, limes, citrus fruits, lemons and grapefruits. The citrus fruits may be any one selected from the group consisting of *Citrus unshiu* Marc. Cv. Miyagawa-Wase, *Citrus unshiu* Marc. var. okitsu, *C. unshiu* "Nichinan 1 you", *Citrus hybrid* "Shiranuhi", *Citrus hybrid* "Setoka", *Citrus hybrid* "Kanpei" and *Citrus hybrid* "Tsunokaori".

As such, the prediction of sugar contents or acidity upon ripening of unripe fruits using the established predictive model of sugar content or acidity of fruits can be utilized in output management or the like of fruits, by predicting qualities of ripe fruits before the fruits become ripe, during growth of fruits. For example, sugar content and acidity information of ripe citrus fruits harvested at the end of November can be predicted from unripe citrus fruits harvested in August. In addition, the prediction method can be also used as data for candidate seed selection based on previous prediction of qualities of a new variety of fruits upon research of the new variety of fruits.

A method of establishing a predictive model of a sugar content or acidity of fruits according to another embodiment of the present invention includes obtaining a sample for measuring spectrum from unripe fruits of a training set (preparation); obtaining Fourier transform infrared spectroscopy (FT-IR) spectral data of the unripe fruits using the sample for measuring spectrum (measurement), pre-processing the FT-IR spectral data to obtain standardized spectral data (standardization), and establishing a predictive model of a sugar content or acidity of fruits that is capable of predicting a sugar content or acidity of ripe fruits from spectral data of unripe fruits using a multivariate statistical analysis tool prepared in a database based on the standardized spectral data and a sugar content or acidity analysis result of ripe fruits measured when unripe fruits of the training set become ripe, under the assumption that the spectral data of the unripe fruits is set as an X variable, and the sugar content or acidity analysis result of ripe fruits measured when the unripe fruits become ripe is set as a Y variable, i.e., $Y_1$ or $Y_2$ (modeling).

Herein, the preparation, measurement and standardization steps have the same entire configurations and features as those described in the prediction method of the sugar content or acidity of fruits only except for samples used and a description thereof will thus be omitted. Specifically, description of these steps is omitted because it is overlapped except for the differences that whether or not the preparation, measurement and standardization steps are applied to unripe fruits (method of predicting a sugar content or acidity of unripe fruits) of a sample having no information about a sugar content or acidity upon ripening, and whether or not the same steps are applied to unripe fruits (method of establishing a predictive model of a sugar content or acidity of unripe fruits) of the training set.

The multivariate statistical analysis tool used in the modeling step is principal component analysis (PCA) and/or partial least squares discriminant analysis (PLS-DA) and may be carried out in an R program using NIPALS algorithms.

Principal component analysis (PCA) can be carried out by obtaining a principal component 1 (PC 1) and a principal component 2 (PC 2) with excellent explanation power from analysis results of analysis subjects, spectrum and a sugar content and acidity, and representing a PCA score plot based on PC 1 and PC 2.

Partial least squares discriminant analysis (PLS-DA) is a multivariate statistical analysis method. The multivariate statistical analysis method models an equation such as Equation 1 using set change and target variables.

$$y=ax_1+bx_2+cx_3+dx_4 \quad \text{[Equation 1]}$$

wherein $x_1$, $x_2$, $x_3$ and $x_4$ are change variables, y is a target variable, and a, b, c and d are constants.

As multivariate statistical analysis, PL is a method of analyzing multivariate data based on correlation between a measured variable and a predictor variable. In Equation 1, the change variable and the target variable correspond to the measured variable and the predictor variable, respectively. In this case, under the assumption that the measured variable is set at x and the predictor variable is set at y, correlation of each of x and y is referred to as regression.

Partial least squares can be used even a case in which the number of predictor variables is greater than the number of measured variables. In this case, a predictive model can be established using multiple correlation between x and y. This feature has an advantage of determining effective relationships between various traits including sugar content and acidity, which are main quality-determining factors of fruits, and prediction thereof, as compared to a case of using a simple regression model.

Specifically, modeling can be conducted as a procedure of establishing a predictive model of a sugar content or acidity of fruits that is capable of predicting a sugar content or acidity of ripe fruits from spectral data of unripe fruits, using a multivariate statistical analysis tool prepared in a database based on the standardized spectral data and an analysis result of a sugar content or acidity of ripe fruits measured when unripe fruits of the training set become ripe, under the assumption that spectral data of unripe fruits is set as an X variable, and the analysis result of a sugar content or acidity of ripe fruits measured when unripe fruits become ripe is set as a Y variable, $Y_1$ or $Y_2$. The established predictive model of the sugar content or acidity of fruits may be further subjected to testing including i) applying spectral data of unripe fruits obtained from unripe fruits of the test set as an X variable to the predictive model of the sugar content or acidity of fruits, ii) obtaining a predicted value of sugar content or acidity as a Y variable, obtained as a result of i), and iii) comparing the predicted value obtained in ii) with a measured value of sugar content or acidity obtained when the unripe fruits of the test set become ripe.

As a result of regression of the predictive model using the test set, the predictive model of the sugar content or acidity of fruits exhibits excellent accuracy, and specifically, the correlation coefficient ($R^2$) of the sugar content is 0.99 and the correlation coefficient ($R^2$) of the acidity is 0.99.

Advantageous Effects

In accordance with the method of predicting a sugar content and acidity of fruits according to the present invention, a sugar content and acidity of ripe fruits can be predicted before harvest using samples of unripe fruits and the predicted sugar content and acidity can be used as data for quality management of fruits, such as output control of fruits, before the fruits become fully ripe. In addition, the predicted sugar content and acidity can be used as data for selection of candidate seeds, so that efficiency of development of new varieties can be improved.

DESCRIPTION OF DRAWINGS

The above and other objects, features and other advantages of the present invention will be more clearly understood from the following detailed description taken in conjunction with the accompanying drawings, in which:

FIG. 1 shows a representative example of FT-IR spectral data measured using samples for measuring spectra of unripe fruits in Example 3 according to the present invention, wherein an arrow represents a significant variation between citrus fruit samples, C represents *Citrus unshiu* Marc. Cv. Miyagawa-Wase, M1 represents mutant line 1, M2 represents mutant line 2, M3 represents mutant line 3, and M4 represents mutant line 4;

FIG. 2 is a graph showing PCA scores as a result of principal component analysis (PCA) of standardized spectral data described in Example 7 of the present invention, wherein a circular dot line represents a boundary of clusters, C represents *Citrus unshiu* Marc. Cv. Miyagawa-Wase, M1 represents mutant line 1, M2 represents mutant line 2, M3 represents mutant line 3, and M4 represents mutant line 4;

FIG. 3 is a graph showing loading value plots of PCA scores as a result of principal component analysis (PCA) of standardized spectral data described in Example 7 of the present invention, wherein an arrow represents an FT-IR region playing a significant role in clustering of FIG. 2, C represents *Citrus unshiu* Marc. Cv. Miyagawa-Wase, M1 represents mutant line 1, M2 represents mutant line 2, M3 represents mutant line 3, and M4 represents mutant line 4;

FIG. 4 is a graph showing a PLS-DA score plot described in Example 7 of the present invention, wherein a circular dot line represents a boundary of clusters of a sample depending on the type of citrus fruits, C represents *Citrus unshiu* Marc. Cv. Miyagawa-Wase, M1 represents mutant line 1, M2 represents mutant line 2, M3 represents mutant line 3, and M4 represents mutant line 4;

FIG. 5 shows a PCA dendrogram analysis result of HCA dendrograms described in Example 7 of the present invention, wherein C represents *Citrus unshiu* Marc. Cv. Miyagawa-Wase, M1 represents mutant line 1, M2 represents mutant line 2, M3 represents mutant line 3, and M4 represents mutant line 4;

FIG. 6 shows a PLS-DA dendrogram analysis result of HCA dendrograms described in Example 7 of the present invention, wherein C represents *Citrus unshiu* Marc. Cv. Miyagawa-Wase, M1 represents mutant line 1, M2 represents mutant line 2, M3 represents mutant line 3, and M4 represents mutant line 4;

FIG. 7 shows evaluation results of prediction degrees with respect to sugar content obtained using PLS modeling for predicting sugar content and acidity according to Example 8 of the present invention, and specifically shows linear regression analysis results (regression correlation coefficient, $R^2=0.99$) between predicted values analyzed using unripe fruits and true values measured using ripe fruits; and FIG. 8 shows evaluation results of prediction degrees with respect to acidity obtained using PLS modeling for predicting sugar content and acidity according to Example 8 of the present invention, and specifically shows linear regression analysis results (regression correlation coefficient, $R^2=0.99$) between predicted values analyzed using unripe fruits and true values measured using ripe fruits.

BEST MODE

Hereinafter, examples of the present invention will be described with reference to the annexed drawings in detail to such an extent that a person having ordinary knowledge in the art to which the present invention pertains can easily implement the examples. However, the present invention can be realized in various forms and is not limited to the examples described herein.

In the present examples, *Citrus unshiu* Marc. Cv. Miyagawa-Wase citrus fruits were used as a control group, and sugar content and acidity were predicted using the control group and mutant varieties of citrus fruits that differ from the control group in terms of sugar content and acidity. The sugar content and acidity of the control group and mutant citrus fruits were measured, FT-IR analysis spectral data were obtained from the control group and mutant citrus fruits and a sugar content and acidity predictive model was developed using multivariate statistical analysis.

Example

1. Preparation of Fruit Materials and Measurement of Sugar Content and Acidity 1-1: Materials: Preparation of Control Group and Mutant Line Samples The citrus fruit varieties used in the present example were *Citrus unshiu* Marc. Cv. Miyagawa-Wase grown most commonly in the Jeju island and mutant lines differing from the control group in terms of sugar content and acidity, induced by irradiation of the *Citrus unshiu* Marc. Cv. Miyagawa-Wase.

The mutant lines were established by creating mutants by irradiation ($^{60}CO$) in the Applied Radiological Science Research Institute, Jeju University and grafting the same to trifoliate orange rootstocks.

At least three to five unripe citrus fruits were collected from each of one variety of *Citrus unshiu* Marc. Cv. Miyagawa-Wase and four mutant lines in August, 2013, and respective unripe citrus fruits were lyophilized and ground into a fine powder using a dried mortar and pestle to obtain a powder sample of unripe citrus fruits. The powder sample of unripe citrus fruits was stored in a −70° C. ultralow-temperature freezer, was used for testing and a part of the unripe citrus fruits was used for measurement of traits. In addition, ripe citrus fruits were harvested from the same trees as the analytic sample of unripe citrus fruits at the end of November, 2013 and were used for measurement of traits while stored in a low-temperature freezer (4° C.)

1-2: Measurement of Sugar Content and Acidity

The sugar content and acidity of unripe and ripe citrus fruits were measured by collecting citrus fruits juices from respective citrus fruits using a juice extractor, allowing the collected citrus fruit juices to pass through a mesh, and feeding about of 4 to 5 mL of the juices to an acidity/sugar content analyzer (NH-2000, HORIBA, Japan) using a 10 mL syringe.

2. Preparation of Sample

Whole-cell lyophilized substances of unripe citrus fruits, as samples for preparing an extract, were prepared using *Citrus unshiu* Marc. Cv. Miyagawa-Wase unripe citrus fruits and four lines of mutant unripe citrus fruits. 20 mg of each of the prepared lyophilized powders was fed to a tube and 200 L of a 20% methanol solution was added thereto and was then thoroughly stirred. Reaction was conducted in the tube in a 50° C. bath for 20 minutes, centrifugation was conducted at 13,000 rpm for 15 minutes and the supernatant was transferred to a new tube. Impurities were removed from the collected supernatant by repeated centrifugation and the supernatant was transferred to a new tube again. The finally collected supernatant was stored at −20° C. and was then used as a sample for measuring spectrum for FT-IR spectrum investigation in the following method.

3. Obtainment of FT-IR Analysis Spectral Data and Mathematical Pre-Processing 3-1: Obtainment of Data Fourier transform infrared (FT-IR) spectral investigation was conducted using Tensor 27 (Bruker Optics GmbH, Ettlingen, Germany) and analysis was conducted using a deuterated triglycine sulfate (DTGS) detector. 5 L of each of the samples for measuring spectrum prepared by the method described in 2 above was fed to a 384-well ZnSe plate and dried on a 37° C. hot plate for about 20 minutes. Spectrum analysis was conducted on the dried ZnSe plate using HTS-XT (Bruker Optics GmbH) high-efficiency automatic equipment provided in the Tensor 27.

The spectrum of each sample was repeatedly measured at an interval of 4 $cm^{-1}$ 128 times in total within the range of 1,800 to 800 $cm^{-1}$ in total, and FT-IR spectrum of the sample was measured three times for statistical analysis. The average spectrum of the results was used as FT-IR spectral data in the subsequent analysis. The program used for FT-IR spectral investigation and data conversion was OPUS Lab available from Bruker (ver. 6.5, Bruker Optics Inc.).

3-2: Mathematical Pre-Processing of Data

For multivariate statistical analysis of FT-IR spectral data, first, pre-processing of spectrum such as baseline correction, normalization and mean centering of FT-IR spectral data was conducted using an R program (version 2.15.0, Auckland, New Zealand).

Absorbance at both end points (1,800 and 800 $cm^{-1}$) of the FT-IR spectrum analysis region were adjusted to zero for baseline correction and spectrum was normalized to the same area to minimize experimental errors. Then, pre-processing of spectral data was completed by mean centering of data and then quadratic differential processing.

Representative FT-IR spectral data is shown in FIG. 1 and multivariate statistical analysis was conducted using the standardized spectral data which had been subjected to mathematical pre-processing described above in the subsequent process.

4. Sugar Content and Acidity Predictive PLS Modeling

Standardized spectral data were obtained by principal component analysis (PCA) and partial least squares discriminant analysis (PLS-DA) (Fiehn et al., 2000. Nat. Biotechnol. 18:1157-1161; Trygg et al., 2007. J. Proteomes Res. 6:467-479.) in a R program (version 2.15.0) using NIPALS algorithms (Wold, H. 1966. Estimation of principal components and related models by iterative least squares, p. 391-420. In: K. R. Krishnaiah (ed.). Multivariate Analysis. Academic Press, New York).

Hierarchical clustering analysis (HCA) was conducted using scores obtained by PCA and PLS-DA, and the relationship between the samples is shown as a dendrogram by measuring a Euclidean distance using an unweighted pair group method with arithmetic mean analysis (UPGMA) as a similarity index.

In addition, a sugar content and acidity predictive model was developed from standardized spectral data of citrus fruit samples and then compared with measured values to test (verify) the accuracy of the predictive model. The predictive model was established using actually measured sugar content and acidity quantitative data of ripe citrus fruits that have the same varieties and lines as one variety of *Citrus unshiu* Marc. Cv. Miyagawa-Wase and four lines of mutant unripe citrus fruits which had been subjected to measurement of FT-IR spectral data, and the standardized spectral data was used as the X variable and sugar content and acidity quantitative data measured using the acidity and sugar content analyzer (NH-2000, HORIBA, Japan) were used as two Y variables.

Partial least squares regression (PLSR) analysis was conducted using a R program (version 2.15.0). In order to improve the accuracy of the predictive modeling, cross-validation of two Y variables with respect to one X variable was conducted.

Sugar content and acidity upon ripening of citrus fruit samples were predicted using established predictive modeling and analytical samples obtained from unripe fruits. In addition, in order to investigate the accuracy of sugar content and acidity predictive modeling, correlation coefficients were investigated by conducting linear regression with respect to true values and predicted values of sugar content and acidity from citrus fruit samples.

5. Investigation Results of Sugar Content and Acidity of Unripe Citrus Fruits and Ripe Citrus Fruits The sugar content and acidity of unripe citrus fruits (August) and ripe citrus fruits (November) were investigated by the method suggested in 1-2 above and results are shown in the following Table 1.

TABLE 1

| Sample | Number | August | | November | |
| --- | --- | --- | --- | --- | --- |
| | | Sugar content (°Brix) | Acidity (%) | Sugar content (°Brix) | Acidity (%) |
| C | 5 | 6.2 ± 0.13 | 2.19 ± 0.03 | 8.4 ± 0.42 | 0.64 ± 0.04 |
| M1 | 5 | 6.2 ± 0.29 | 1.82 ± 0.08 | 10.3 ± 1.88 | 0.99 ± 0.25 |
| M2 | 5 | 6.2 ± 0.53 | 1.81 ± 0.08 | 8.4 ± 0.23 | 0.79 ± 0.08 |
| M3 | 5 | 6.3 ± 0.38 | 2.09 ± 0.16 | 9.7 ± 0.83 | 0.61 ± 0.06 |
| M4 | 5 | 6.3 ± 0.26 | 1.75 ± 0.07 | 9.5 ± 0.18 | 0.65 ± 0.03 |

[C: *Citrus unshiu* Marc. Cv. Miyagawa-Wase, M1, mutant line 1; M2, mutant line 2; M3, mutant line 3; M4, mutant line 4]

As can be seen from Table 1 above, the overall sugar content of unripe citrus fruit samples collected in August was 6.2 to 6.3° Brix. At this time, sugar content was low and there was no difference between the samples because moisture was evaporated from citrus fruits and sugar was accumulated. In addition, the M4 line showed the lowest acidity of 1.75%, and *Citrus unshiu* Marc. Cv. Miyagawa-Wase showed the highest acidity of 2.19%. There was a significant difference in acidity, rather than sugar content, between the unripe citrus fruits of mutant lines and unripe citrus fruits of *Citrus unshiu* Marc. Cv. Miyagawa-Wase.

In addition, regarding ripe citrus fruit samples harvested in November, the M1 line had a sugar content of 10.3° Brix, which was about 2° Brix higher than the sugar content, 8.4° Brix, of *Citrus unshiu* Marc. Cv. Miyagawa-Wase, and which was the highest sugar content among investigated citrus fruit samples. The M2 sample exhibited a sugar content of 8.4° Brix, similar to that of *Citrus unshiu* Marc. Cv. Miyagawa-Wase, and M3 and M4 samples exhibited 9.7 and 9.5° Brix, respectively, which are about 1° Brix higher than that of *Citrus unshiu* Marc. Cv. Miyagawa-Wase citrus fruits. There was also a difference in acidity between *Citrus unshiu* Marc. Cv. Miyagawa-Wase citrus fruits and mutant line citrus fruits. The ripe *Citrus unshiu* Marc. Cv. Miyagawa-Wase and M1 exhibited an acidity of 0.64% and 0.99%, respectively, which were lower than 1%, and ripe M2, M3 and M4 exhibited an acidity of 0.79, 0.61 and 0.65%, respectively, which were lower than 1%. Regarding ripe citrus fruits, *Citrus unshiu* Marc. Cv. Miyagawa-Wase citrus fruits and M2 citrus fruits exhibited similar overall sugar content and acidity, and M1, M3 and M4 exhibited relatively high sugar content and acidity.

These results showed that mutant lines of citrus fruits exhibited a higher sugar content and a lower acidity than *Citrus unshiu* Marc. Cv. Miyagawa-Wase citrus fruits, which means that mutant varieties are relatively valuable.

6. FT-IR Analysis Spectral Data Obtained Using Analytical Sample

Standardized spectral data was obtained by pre-processing of FT-IR spectral data of the whole-cell extract from unripe citrus fruits and a system to distinguish sugar content and acidity was established by conducting multivariate statistical analysis.

As can be seen from results shown in FIG. 1, which are standardized spectral data of citrus fruit samples, samples for measuring spectrum of unripe citrus fruits underwent great quantitative and qualitative pattern changes of metabolites in regions of 1,700-1,500, 1,500-1,300 and 1,100-950 $cm^{-1}$ on the FT-IR spectrum. The regions of 1,700-1,500, 1,500-1,300 and 1,100-950 $cm^{-1}$ on the FT-IR spectrum reflect qualitative and quantitative information of amide bonds I and II between amino acids and proteins, phosphodiester bonds between nucleic acid and phosphatide, organic acids containing phosphorous, and carbohydrate-based compounds including monosaccharides or complex polysaccharides. That is, it can be seen from FT-IR spectral data that there were significant qualitative and quantitative differences between amino acids, or proteins, fatty acids and carbohydrate-based compounds contained in unripe citrus fruits.

7. Multivariate Statistical Analysis Results of Standardized Spectral Data 7-1. PCA Score Analysis Result Regarding PCA scores, which are the principal component analysis (PCA) results of standardized spectral data, PC 1 and PC 2 scores had an explanation power of 63.4%, and 15.5%, respectively, of the total variance, which corresponds to about 78.9% of the total variance. Observation results of the PCA score plot based on PC1 and PC2 with high explanation power are shown in FIG. 2. As can be seen from FIG. 2, citrus fruit samples are broadly divided into upper and lower parts based on PC 2.

Specifically, the citrus fruit samples are disposed in upper and lower parts based on the score group of *Citrus unshiu* Marc. Cv. Miyagawa-Wase on the PCA score plot. The M2 line score group having a similar sugar content to *Citrus unshiu* Marc. Cv. Miyagawa-Wase is distributed together with the *Citrus unshiu* Marc. Cv. Miyagawa-Wase score group, M3- and M4 line score groups are predominantly disposed in lower and upper parts, and the M1 line score group having the highest sugar content is disposed between the M2 and M3 line score groups.

7-2. Analysis Result of Correlation Between PCA Scores and Sugar Content and Acidity of Ripe Fruits To ascertain biological information obtained from spatial distributions and positions on the PCA score plot of unripe citrus fruit samples, first, correlation between differences in sugar content and acidity between ripe citrus fruit samples (Table 1) and positions of the samples on the PCA score plot was investigated.

The sample having a relatively low sugar content, *Citrus unshiu* Marc. Cv. Miyagawa-Wase citrus fruits, created an additional group in the center of the PCA score plot. On the other hand, M1, the sample having the highest sugar content was distributed while creating an additional group in the middle of M2 and M3 on the PCA score plot. The results showed that spatial distributions and positions on the PCA score plot are closely correlated with sugar contents of the samples.

7-3. Analysis Result of Correlation Between PCA Scores and Sugar Content and Acidity of Ripe Fruits In order to investigate FT-IR spectral sites which play an important role in grouping and clustering of citrus fruit samples depending on sugar content and acidity on the PCA score plot, FT-IR spectral sites which play an important role in determining PC 1 and PC 2 were investigated by loading value analysis and results are shown in FIG. 3.

As can be seen from FIG. 3, FT-IR spectral sites important for determining PC 1 which plays an essential role in dividing upper and lower parts on PCA scores are regions of 1,700 to 1,500 and 1,500 to 1,300 $cm^{-1}$, and PC 2 is predominantly disposed in the region of 1,100 to 950 $cm^{-1}$. These FT-IR spectral sites correspond to regions showing great differences between types or lines in the FT-IR spectral data shown in FIG. 1 as well. PC 2 which has an important role in dividing citrus fruit samples is affected by quantitative and qualitative differences in hydrocarbon-based compounds, and qualitative and quantitative differences of amide I and II, fatty acid and carbohydrate-based compounds play an important role in identifying metabolite levels of citrus fruit samples, and qualitative change of sugar-based primary metabolites is correlated with qualitative and quantitative changes of secondary metabolites.

7-4. PLS-DA Analysis Result

Partial least squares discriminant analysis (PLS-DA) was conducted in the same manner as in 4. described above and results are shown in FIG. 4. In FIG. 4 showing a PLS-DA score plot, circular dot lines represent the cluster boundary of samples depending on the type of citrus fruits.

As can be seen from FIG. 4, PLS-DA analysis offers more clear grouping depending on the type of citrus fruits than PCA analysis. PLS-DA showed a smaller boundary between the respective groups than that of PCA and repeated spheres of samples belonging to the same variety are disposed within each group, which means that PLS-DA has improved identification capacity of citrus fruits than PCA.

The sample having a relatively low sugar content, *Citrus unshiu* Marc. Cv. Miyagawa-Wase citrus fruits, created an additional group in the center on the PCA score plot, and the sample having the highest sugar content, M1 citrus fruits are distributed while creating an additional group with M3 citrus fruits in the upper and left part on the PLS-DA score plot. M2 citrus fruits having a similar sugar content to *Citrus unshiu* Marc. Cv. Miyagawa-Wase citrus fruits are predominantly distributed in similar positions to the *Citrus unshiu* Marc. Cv. Miyagawa-Wase citrus fruits.

These results showed that, similar to PCA, PLS-DA showed close correlation between spatial distributions and positions of these samples, and sugar content and acidity thereof on the score plot of citrus fruit samples, as well.

7-5. HCA Dendrogram Analysis Result

HCA dendrogram analysis results obtained in the same manner as described in 4. above are shown in FIGS. 5 and 6. FIG. 5 is a PCA dendrogram for estimating the relationship between citrus fruits used as samples and FIG. 6 is a PLS-DA dendrogram.

As can be seen from FIG. 5, M1, M2, M3 and M4 are distributed based on the *Citrus unshiu* Marc. Cv. Miyagawa-Wase. This is because M1 to M4 mutant lines were induced by mutation of *Citrus unshiu* Marc. Cv. Miyagawa-Wase. Among them, M1 to M3 exhibited higher relationship with *Citrus unshiu* Marc. Cv. Miyagawa-Wase, as compared to M4.

As can be seen from FIG. 6, the relationship between *Citrus unshiu* Marc. Cv. Miyagawa-Wase and other mutant lines was significantly shown in the PLS-DA dendrogram. There was a strong relationship in traits between *Citrus unshiu* Marc. Cv. Miyagawa-Wase and M2 line, and there was a strong relationship in traits between M1 and M3 lines. However, similar to PCA results, M4 had a weak trait relationship. Trait expression was changed depending on mutant induction, which means that the relationship between lines can be estimated based thereon.

8. PLS Regression Predictive Modeling for Predicting Sugar Content and Acidity and Evaluation of Prediction Degree PLS modeling for predicting a sugar content and acidity was developed using FT-IR spectral data and sugar content and acidity data measured using an acidity/sugar content analyzer.

Among unripe citrus fruits harvested in August, 15 citrus fruit samples were prepared for each type of citrus fruits as a training set and spectral data of unripe citrus fruits were obtained in the same manner as above. In addition, ripe citrus fruit samples that are the same as unripe citrus fruit samples of the training set were harvested in January and sugar content and acidity thereof were measured to obtain measured values of sugar content and acidity of the ripe citrus fruit samples.

A predictive model of sugar content or acidity of fruits was prepared in the same statistical analysis manner as described above using the data of training set and was stored in a database. At this time, modeling was conducted by setting spectral data of the unripe citrus fruits as an X variable and the sugar content or acidity as Y a variable, $Y_1$ or $Y_2$.

Then, 10 samples for each type of citrus fruits, among unripe citrus fruits harvested in August, were prepared as a test set, an X variable was obtained in the same manner as above and was applied to the predictive model of the sugar content or acidity of fruits to obtain a predicted value, Y' ($Y_1'$ or $Y_2'$) corresponding to sugar content or acidity values when the unripe citrus fruit samples become ripe, the predicted value was compared with sugar content or acidity values actually measured when unripe citrus fruits of the test set became ripe, and linear regression was conducted to verify the accuracy of the predictive model.

A prediction degree was evaluated using the predicted values using the sugar content and acidity predictive PLS modeling and the true values, and the result is shown in FIGS. 7 and 8. As can be seen from FIGS. 7 and 8, as a result of regression using predicted sugar content and acidity values from FT-IR spectral data of unripe citrus fruits and measured sugar content and acidity values of ripe citrus fruits, both sugar content and acidity exhibited a high correlation coefficient of $R_2=0.99$. These results showed that, only using FT-IR spectral data of unripe citrus fruit samples, sugar content and acidity present in citrus fruit samples when the unripe citrus fruits become ripe can be predicted at an accuracy of about 90%. In addition, this method is greatly essential in that the systemic prediction of sugar content and/or acidity for evaluating the taste of fruits is possible, rather than information about a single ingredient such as sucrose or the like.

These results mean that sugar content and acidity of unripe fruits before harvest can be previously confirmed. Accordingly, the sugar content and acidity predictive modeling according to the present invention can be used to predict sugar content and acidity of ripe fruits more easily and rapidly, and to manage output, qualities and the like, of fruits.

In addition, the sugar content and acidity predictive modeling of fruits according to the present invention can be used as a means for evaluating qualities and characteristics from a number of fruit samples which are not yet subjected to identification and standardization, and as a means for early evaluation of qualities of fruits or for rapidly selecting excellent fruits lines.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention provides data for controlling qualities of fruits based on predicted sugar content and acidity values, and data for selecting candidate seeds for developing new varieties of fruits.

The invention claimed is:

1. A method of simultaneously predicting a sugar content and acidity of citrus fruits comprising:
    preparation of obtaining a sample for measuring spectrum from unripe citrus fruits;
    measurement of obtaining Fourier transform infrared spectroscopy (FT-IR) spectral data of the unripe citrus fruits using the sample for measuring spectrum;
    standardization of pre-processing the FT-IR spectral data to obtain standardized spectral data, and
    prediction of applying the standardized spectral data of unripe citrus fruits to a predictive model of a sugar content and acidity based on multivariate statistical analysis previously prepared in a database to output a predicted value corresponding to a sugar content and acidity when the unripe citrus fruits become ripe,
    wherein the predictive model of sugar content and acidity is established by applying data of a training set to partial least squares (PLS) modeling,
    wherein the pre-processing in the standardization comprises:
    correcting an analysis region and a baseline of the FT-IR spectral data of unripe citrus fruits to be identical to an analysis region and a baseline of spectral data of the training set applied to the establishment of the predictive model of the sugar content and acidity;
    normalizing an area of the corrected FT-IR spectral data of unripe citrus fruits to be identical to an area of the spectrum applied to the training set; and
    conducting mean centering and quadratic differential processing on the normalized FT-IR spectral data of unripe citrus fruits to obtain spectral data of unripe citrus fruits,
    wherein the correcting baseline of the FT-IR spectral data of unripe citrus fruits comprises adjusting an absorbance at both end points (1,800 and 800 cm$^{-1}$) of a FT-IR spectrum analysis region to zero,
    wherein the FT-IR spectral data of unripe citrus fruits is measured at an interval of 4 cm$^{-1}$ in an analysis region including a region of 1,800 to 800 cm$^{-1}$,
    wherein the simultaneous prediction of the sugar content and acidity of citrus fruits is performed during the growth of fruits.

2. The method according to claim 1, wherein the predictive model of sugar content and acidity established using the training set is established by applying the spectral data of unripe citrus fruits to an X variable and a sugar content and acidity of ripe citrus fruits measured when the unripe citrus fruits become ripe to a Y variable, $Y_1$ or $Y_2$, respectively.

3. The method according to claim 1, wherein a predicted value of sugar content and acidity upon ripening of unripe citrus fruits output in the prediction has an accuracy of 90% or more.

4. A method of establishing a simultaneously predictive model of a sugar content and acidity of citrus fruits comprising:
    preparation of obtaining a sample for measuring spectrum from unripe citrus fruits of a training set;
    measurement of obtaining Fourier transform infrared spectroscopy (FT-IR) spectral data of the unripe citrus fruits using the sample for measuring spectrum;
    standardization of pre-processing the FT-IR spectral data to obtain standardized spectral data; and
    modeling of establishing a predictive model of a sugar content and acidity of citrus fruits for predicting a sugar content and acidity of ripe citrus fruits from spectral data of unripe citrus fruits, using a multivariate statistical analysis tool prepared in a database based on the standardized spectral data and a sugar content and acidity analysis result of ripe citrus fruits measured when unripe citrus fruits of the training set become ripe, under the assumption that spectral data of the unripe citrus fruits is set as an X variable, and the sugar content and acidity analysis result of ripe citrus fruits measured when the unripe citrus fruits become ripe is set as a Y variable, i.e., $Y_1$ and $Y_2$,
    wherein the FT-IR spectral data of unripe citrus fruits is measured at an interval of 4 cm$^{-1}$ in an analysis region including a region of 1,800 to 800 cm$^{-1}$.

5. The method according to claim 4, further comprising testing, wherein the testing comprises:
    i) applying spectral data of unripe citrus fruits obtained from the unripe citrus fruits of the test set as an X variable to the predictive model of the sugar content and acidity of citrus fruits;
    ii) obtaining a predicted value of sugar content and acidity as a Y variable, obtained as a result of i); and
    iii) comparing the predicted value obtained in ii) with a measured value of sugar content and acidity obtained when the unripe citrus fruits of the test set become ripe.

* * * * *